US006547072B2

(12) United States Patent
Whiting et al.

(10) Patent No.: US 6,547,072 B2
(45) Date of Patent: Apr. 15, 2003

(54) STACKABLE GUIDEWIRE HOLDER

(75) Inventors: John Whiting, Salt Lake City, UT (US); Jim Mottola, South Jordan, UT (US); Fred Lampropoulos, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 169 days.

(21) Appl. No.: 09/846,677

(22) Filed: Apr. 26, 2001

(65) Prior Publication Data

US 2002/0157981 A1 Oct. 31, 2002

(51) Int. Cl.[7] .............................................. B65D 83/10
(52) U.S. Cl. ........................ 206/364; 206/210; 206/438; 206/509
(58) Field of Search ................................ 206/363, 364, 206/369, 210, 408, 409, 438, 389, 509; 600/585; 604/171

(56) References Cited

U.S. PATENT DOCUMENTS

| 3,384,140 A | * | 5/1968 | Brothers ...................... 206/389 |
| 3,390,844 A | * | 7/1968 | Dillow et al. ................ 206/409 |
| 4,475,652 A | * | 10/1984 | Heard .......................... 206/409 |
| 4,915,216 A | | 4/1990 | Magers ........................ 206/520 |
| 4,936,448 A | | 6/1990 | Holloway .................... 206/364 |
| D364,564 S | | 11/1995 | Moore .......................... D9/429 |
| D369,717 S | | 5/1996 | Chiba ........................... D7/354 |
| 5,611,428 A | | 3/1997 | Banerian ..................... 206/364 |
| 5,634,570 A | * | 6/1997 | Casper et al. ............... 206/408 |
| 5,738,213 A | | 4/1998 | Whiting et al. ............. 206/364 |
| 5,769,222 A | | 6/1998 | Banerian ..................... 206/364 |
| 6,047,825 A | | 4/2000 | Samuels ...................... 206/364 |
| 6,068,121 A | * | 5/2000 | Mcglinch .................... 206/364 |
| D433,130 S | | 10/2000 | Cude et al. ................. D24/121 |

* cited by examiner

Primary Examiner—Luan K. Bui
(74) Attorney, Agent, or Firm—Workman, Nydegger & Seeley (57) ABSTRACT

A guidewire holder is provided that stores a coiled guidewire substantially immersed in a storage fluid and allows for a facilitated retrieval of the guidewire. The guidewire holder is generally configured as a shallow pan in a circular shape with an outer periphery to retain the coiled guidewire. The outer periphery includes a concave inner wall and a set of ribs that generally retain the coiled guidewire on the outer periphery. An access area is provided to suspend a portion of the guidewire away from the outer periphery to enable a medical practitioner to reach into the guidewire holder and grasp a portion of the guidewire in order to easily extract the coiled guidewire from the holder. An inner periphery reduces the amount of storage fluid needed to immerse the guidewire and is used in combination with the outer periphery to provide a location for comfortably holding the guidewire holder. Multiple holders may be coupled together so as to be stacked on top of each other.

37 Claims, 5 Drawing Sheets

STACKABLE GUIDEWIRE HOLDER

BACKGROUND OF THE INVENTION

1. The Field of the Invention

The present invention relates to a stackable holder for storage and retrieval of a coiled wire. More specifically, the present invention is directed to a stackable holder for storage and retrieval of a coiled medical guidewire, wherein the stackable holder facilitates the extraction of the coiled guidewire from the holder.

2. Background and Related Art

Guidewires are used in the medical profession to direct a catheter to an identified site within a cardiovascular or peripheral vascular system of a patient for the purpose of diagnosis and/or treatment. The guidewire is typically placed into a blood vessel of the patient and is directed by a medical practitioner to the identified site of the patient's body. A catheter is then advanced over the guidewire until the functional structure of the catheter is located in proximity to the identified site. The catheter is then utilized to accomplish the selected medical procedure. The guidewire is withdrawn from the patient's body before, during, or after utilization of the catheter.

A specific example of the utilization of a guidewire in the medical profession is provided in the procedure for directing an angiographic catheter to the site of a vascular obstruction of a patient's body. Once a guidewire is inserted and located at the site of the vascular obstruction, an angioplasty catheter, such as a balloon angioplasty catheter, is advanced over the guidewire to the site of the obstruction. The balloon is then inflated to reduce or eliminate the obstruction. Guidewires are also used in many other medical procedures, including procedures that provide an application of ultrasound, a delivery of medication, an execution of a diagnostic procedure, etc. Additionally, medical procedures exist that require the utilization of more than one guidewire during the procedure.

To prepare the guidewires for use in a medical procedure, the guidewires are typically removed from any transport packaging and/or containers and are placed into an open storage tray that is filled with a storage fluid, such as a heparin solution. When a guidewire is needed, a medical practitioner reaches into the open storage tray, grasps a guidewire, and removes it from the storage fluid.

While storage trays are currently available for medical guidewires, many problems exist from the utilization of the available storage trays. For example, guidewires are often several feet in length and therefore are typically coiled before being placed in the storage tray. However, due to the resiliency of the materials used to form the guidewires, the guidewires generally uncoil until they touch a sidewall of the storage tray. This increases the difficulty for a practitioner to grasp a guidewire and remove it from the tray. When a practitioner reaches into the storage tray, the surgical gloves worn by the practitioner further increase the difficulty of grasping a portion of the guidewire since the diameter of a guidewire generally only ranges from 0.011 to 0.030 inches. Furthermore, when multiple guidewires are placed within a storage tray, the guidewires tend to uncoil until they touch a sidewall of the storage tray and thus create even more of a challenge for the practitioner to identify and remove a particular guidewire from the tray.

Some guidewires are coated with a hydrophilic coating in order to facilitate the process of passing a guidewire through a body vessel and passing a catheter over the guidewire. These coatings tend to make the guidewire "slippery." When such a guidewire is required, it is very difficult for a practitioner to grasp a portion of the guidewire and remove it from the storage tray while wearing surgical gloves. This is particularly true where the guidewire has sprung open so as to rest firmly against the sides of the storage tray.

Other problems associated with currently available storage trays include retaining a guidewire immersed in the storage fluid. As provided above, once a guidewire is coiled and placed into a storage tray, the guidewire generally uncoils until it touches a sidewall of the storage tray. Some storage trays have sidewalls that slope slightly outward (e.g., the inside angle formed between the sidewalls and the bottom of the storage tray is obtuse). Therefore, if the storage tray is bumped, the guidewire may work its way up the sides of the tray and spring out of the tray.

In order to overcome some of the problems associated with storing guidewires, one guidewire holder was developed that is formed from a coiled tube and is filled with a storage fluid. The end of the coiled tube is bent into a vertical position and flared. Guidewires are fed through the opening and around the coils so as to be submersed in the storage fluid. However, the guidewire storage tube requires the end of the guidewire to extend out of the coiled tube to allow a practitioner to grasp the end and remove the guidewire from the storage unit. As such, the end of the guidewire is exposed to the atmospheric air instead of residing underneath a storage fluid, thereby increasing the likelihood of the guidewire becoming contaminated before it is used in the medical procedure.

SUMMARY OF THE INVENTION

The present invention relates to a stackable holder for storage and retrieval of a coiled wire. More specifically, the present invention is directed to a stackable holder for storage and retrieval of a coiled medical guidewire, wherein the stackable holder facilitates the extraction of the coiled guidewire from the holder.

The present invention comprises various implementations that are capable of storing a coiled wire that has a natural tendency to spring open. One implementation includes a holder that is used for storage and retrieval of a coiled guidewire. The guidewire holder is generally configured as a shallow pan in a circular shape that includes an outer periphery to retain a coiled guidewire in the pan. The periphery includes a set of ribs that facilitate maintaining the coiled guidewire substantially immersed in storage fluid to prevent contamination of the guidewire.

The guidewire holder may include an inner periphery that reduces the amount of storage fluid required to immerse the coiled guidewire. In addition, the combination of the inner periphery and outer periphery form a handle for which a user, such as a medical practitioner, may comfortably grasp the guidewire holder.

The guidewire holder may also include one or more access areas that, in combination with the set of ribs, provide easy access to the coiled guidewire. In a further implementation of the present invention, the access area includes a nose portion of the outer periphery that protrudes out to perform the function of providing an area where at least a portion of the guidewire is suspended so as to not touch at least the outer periphery. The access area allows a medical practitioner to easily grasp the coiled guidewire retained in the holder in order to remove it from the guidewire holder.

The guidewire holder may be coupled with another guidewire holder so that the guidewire holders are stacked.

In a further implementation of the present invention, a rim of the outer periphery of a first guidewire holder and a stacking groove formed on the bottom surface of a second guidewire holder have a corresponding size and shape that allow the rim of the first guidewire holder to be coupled to the stacking groove of the second guidewire holder, thereby allowing the second guidewire holder to be stacked on top of the first guidewire holder.

Additional features and advantages of the present invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

The present invention relates to a stackable holder for storage and retrieval of a coiled wire. More specifically, the present invention is directed to a stackable holder for storage and retrieval of a coiled medical guidewire, wherein the stackable holder facilitates the extraction of the coiled guidewire from the holder.

The embodiments of the present invention comprise a means for defining a pan to hold a coiled wire, which has a natural tendency to spring open, and a means for retaining the coiled wire within the pan, wherein the means for retaining the coiled wire is formed in the outer periphery of the pan. While the exemplary embodiment of the present invention illustrated in FIGS. 1–5 is directed to a holder of a medical guidewire, embodiments of the present invention embrace holders of any type of wire or cord that can be coiled and that has a natural tendency to spring open.

Figure 1:
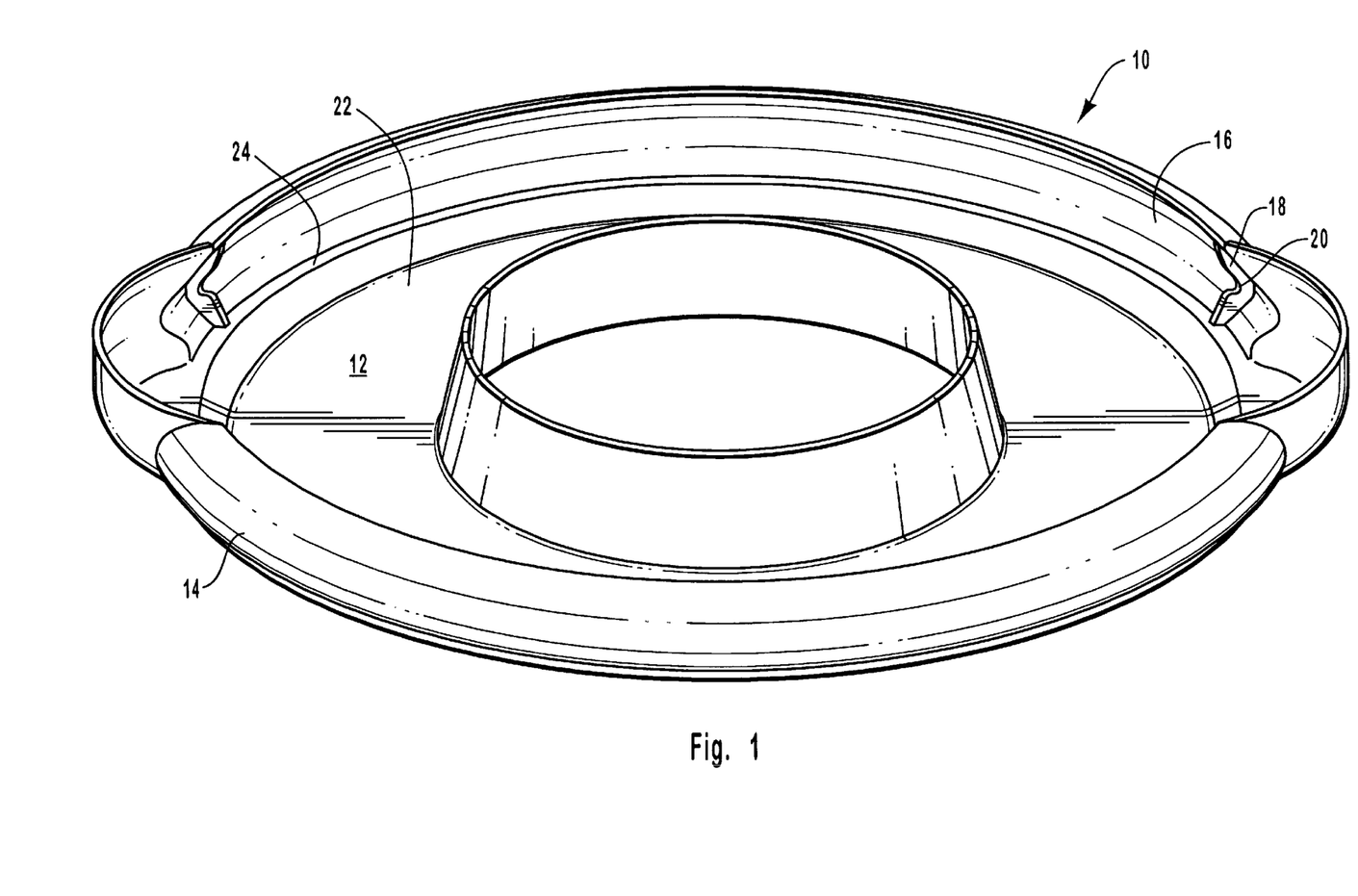
FIG. 1 is a perspective view of one embodiment of the present invention.

With reference to FIG. 1, a perspective view is provided of an embodiment of the present invention. The illustrated embodiment is a medical guidewire holder that comprises a means for defining a pan, which holds a coiled guidewire, and a means for retaining the coiled guidewire within the pan. An example of a means for defining a pan includes the shape illustrated in FIG. 1. Furthermore, an example of a means for retaining a coiled guidewire includes an outer periphery of the pan, as will be further explained below. The guidewire holder may comprise a variety of materials including plastic, metal, ceramic, etc. and may be formed by a variety of different manufacturing processes, including an injection molding process, a die process, etc.

In FIG. 1, the illustrated embodiment is provided as medical guidewire holder 10, which comprises a means for defining a pan, illustrated as pan 12. While the illustrated embodiment provides a generally circular shape for pan 12, embodiments of the present invention embrace a variety of shapes to hold a coiled wire, including an oval, triangular, or rectangular shaped pan.

As explained above, embodiments within the scope of the present invention also comprise a means for retaining a coiled wire. For example, in FIG. 1 such means for retaining comprises an outer periphery 14 of pan 12 that is sized and shaped so as to retain a coiled guidewire (not shown) therein. The outer periphery 14 may include one or more ribs 18 for retaining the coiled guidewire within the pan 12 and for facilitating an extraction or removal of the guidewire from the holder 10, as will be further explained below. Furthermore, the means for retaining may hold the guidewire substantially immersed in storage fluid when the storage fluid is placed in the pan 12.

In one embodiment, and as illustrated in FIG. 1, outer periphery 14 is curved inward to present a concave inner wall 16 to retain a guidewire (not shown). Since guidewires that are coiled have a natural tendency to spring open, the presentation of the concave inner wall 16 to the coiled guidewire causes the spring force of the guidewire to retain the guidewire within the outer periphery 14 of the pan 12. One or more ribs 18, located in the outer periphery 14 of the pan 12, further assist in retaining the guidewire within the pan 12. Each rib 18 has a slot 20 for receiving a portion of the coiled guidewire. Thus, the combination of the concave inner wall 16, the one or more ribs 18, and the spring force of the guidewire retain the guidewire within the pan 12.

A medical guidewire is often stored in a storage fluid, such as a heparin solution, to prevent contamination of the guidewire. As such, the means for retaining of the present invention may be used to hold the medical guidewire substantially immersed in the storage fluid when storage fluid is placed in the pan. The means for retaining further prevents the guidewire from working its way out of the guidewire holder 10 prior to a medical practitioner removing the guidewire from the guidewire holder 10.

In the illustrated embodiment, the floor of pan 12 comprises an annular channel 22 and an annular ridge 24. The ridge 24 is interposed between the channel 22 and the outer periphery 14. The annular ridge 24 corresponds to a stacking groove (not shown) located on the underneath surface of the pan 12 that facilitates the stacking of multiple guidewire holders, as will be further explained below. The stacking groove also provides aerodynamics to the holder 10 should the holder 10 be used for recreation purposes. Furthermore, the open construction of pan 12 facilitates the cleaning, inspection, etc. of the guidewire holder 10.

Figure 2:
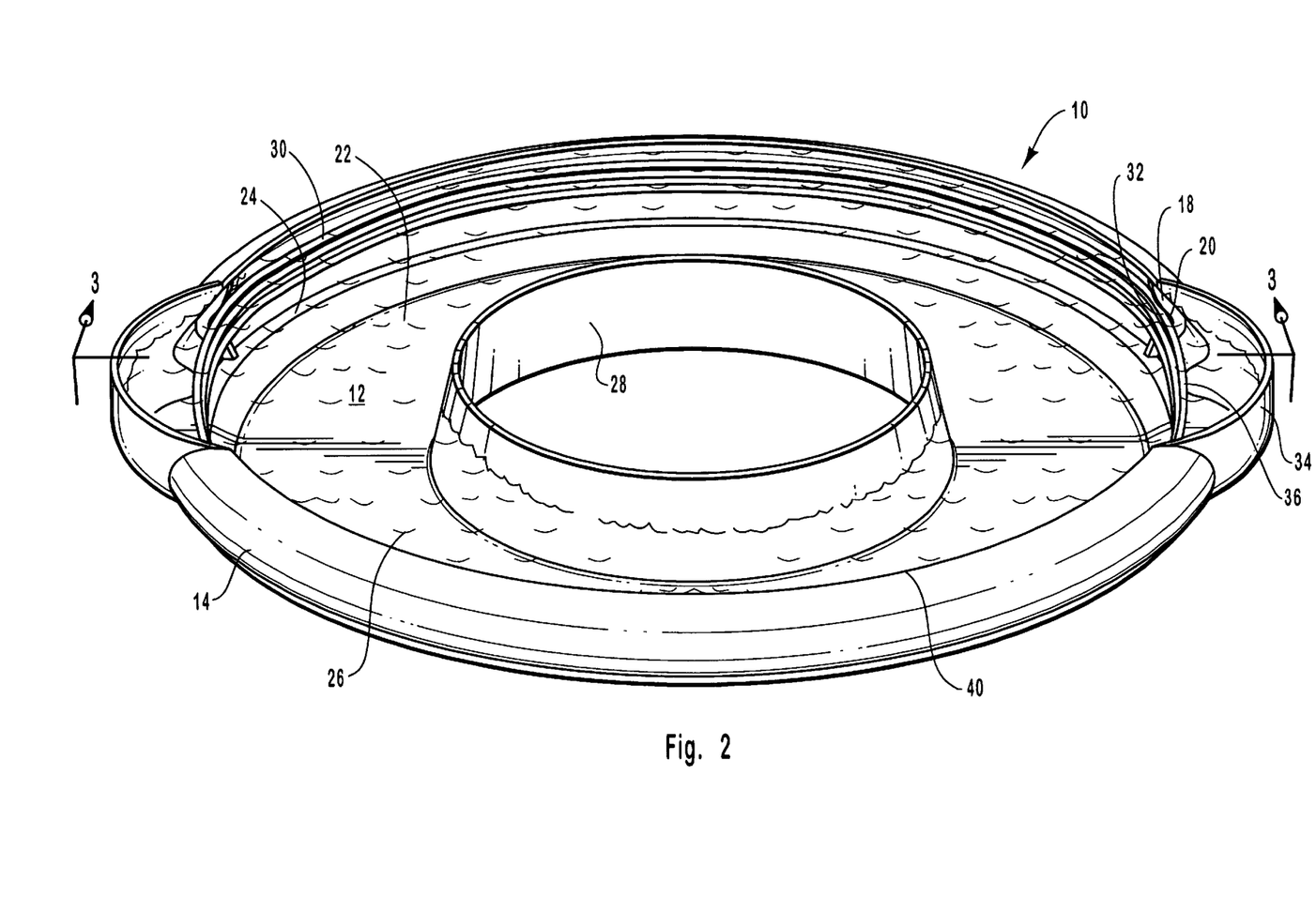
FIG. 2 is a perspective view of the embodiment of FIG. 1 retaining a guidewire and holding storage fluid therein.

Referring now to FIG. 2, a perspective view is illustrated of the guidewire holder of FIG. 1 retaining a coiled guidewire and holding storage fluid therein. As provided above, the guidewire 30 is substantially immersed in storage fluid 26, such as a heparin solution, to prevent contamination.

In order to reduce the amount of storage fluid 26 that is required to fill the guidewire holder 10, embodiments within the scope of the present invention may comprise an inner periphery 28 of pan 12. The inner periphery 28 may have a variety of structures, including a vertical, curved or tapered wall. In the illustrated embodiment, the structure of inner periphery 28 is slightly tapered to present an outward canted surface with respect to channel 22. Furthermore, the combination of an outward canted inner periphery 28 and a curved outer periphery 14 provides an example of a means for holding by providing a handle for comfortably grasping the guidewire holder 10.

As provided above, the illustrated embodiment includes an outer periphery 14 that comprises a concave inner wall and one or more ribs that retain the guidewire holder within pan 12, substantially immersed within storage fluid 26. Since a coiled guidewire has a natural tendency to spring open, the presentation of the concave inner wall to the coiled guidewire causes the spring force of the guidewire to force the guidewire to be retained on the outer periphery 14. As illustrated in FIG. 2, the coiled guidewire 30 generally resides at the concave inner wall of the outer periphery 14, and a slot 20 of a rib 18 receives a portion 32 of the guidewire 30. This causes the coiled guidewire 22 to be submersed in storage fluid 26 and helps to prevent the guidewire 30 from working its way out of the storage solution 26 and out of guidewire holder 10 prior to a medical practitioner removing the guidewire 30 from the holder 10.

Embodiments of the present invention may comprise one or more means for providing access to the coiled guidewire. By way of example, and not limitation, the illustrated embodiment provides a nose portion 34 in combination with a set of ribs 18 as an example for a means for providing access to the coiled guidewire 30. The primary function of any access area included within the present invention is to allow a medical practitioner to easily grasp a coiled guidewire 30 that is stored within the guidewire holder 10. As illustrated in FIG. 2, nose portion 24 in combination with a set of ribs 18 provide an area where at least a portion 36 of the coiled guidewire 30 is suspended so as to not touch the outer periphery 14 of pan 12. The set of ribs 18 are located so that a first rib is located near a first end of nose portion 34 and a second rib is located near a second end of nose portion 34. As such, a portion 36 of the guidewire is suspended away from the outer periphery 14 of the pan 12. The portion 36 is also held above the ridge 24. In other words, in FIG. 2, the nose portion 34 in combination with a set of ribs 18 provides an area wherein a portion 36 of the guidewire does not contact any inside surface of the pan 12. By suspending at least a portion 36 of the guidewire 30 away from the outer periphery 14, a medical practitioner can easily reach into the guidewire holder 10, grasp onto the suspended portion 36, and remove the guidewire 30 from the guidewire holder 10.

While the illustrated embodiment provides a curved nose portion 34, other shapes may be used to suspend at least a portion of the guidewire away from the outer periphery and/or the ridge. Furthermore, while the illustrated embodiment provides two access areas, embodiments of the present invention embrace holders that comprise less than two access areas or more than two access areas.

Figure 3:
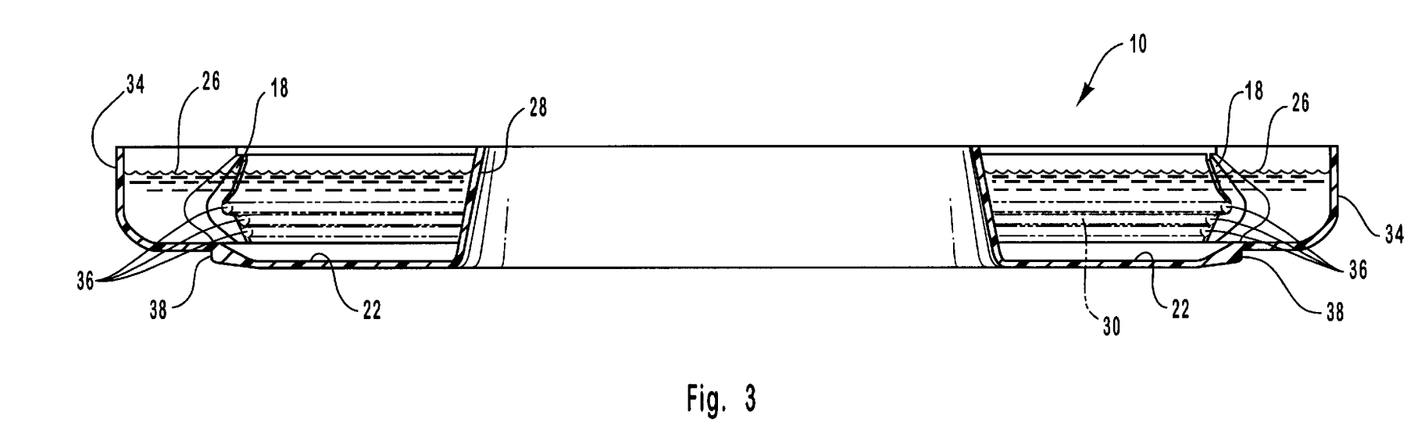
FIG. 3 is a cross-sectional view taken along the line 3—3 of FIG. 2.

As provided above, the outer periphery 14 creates a structure that retains the coiled guidewire 30 within the guidewire holder 10 and keeps the coiled guidewire 30 off of the surface of the channel 22. This function is perhaps best illustrated in FIG. 3, which is a cross-sectional view taken along the line 3—3 of FIG. 2. As provided above, the guidewire generally resides on the concave inner wall of the outer periphery of the pan. A portion of the guidewire is held by a slot of a rib 18 so as to retain the guidewire within the pan and to hold a portion 36 of the guidewire 30 suspended away from the outer periphery of the pan to facilitate the removal of the guidewire 30 from the holder 10. By providing such a structure, the coiled guidewire is kept generally submerged under the storage fluid 26 and a portion 36 is suspended away from an inner surface of the holder 10. This causes the guidewire to be more easily grasped by a medical practitioner and removed from the guidewire holder. As illustrated in FIG. 3, the nose portion 24 also assists to cause a portion 36 of the guidewire 30 to be suspended away from an inner surface of the holder 10 to facilitate the removal of the guidewire 30 from the guidewire holder 10. Such a combination of a nose portion 34 and a set of ribs 18 are an example of the implementation of a means for providing access to a coiled guidewire.

FIG. 3 also provides a view of a means for retaining a coiled guidewire substantially immersed in the storage fluid. The illustrated means for retaining comprises the concave inner wall of outer periphery 14 and the set of ribs 18 at each access area.

Embodiments of the present invention may also comprise a means for stacking the guidewire holder to other such guidewire holders so that the guidewire holders can be stacked on top of each other and be maintained in the stacked configuration. For example, such means for stacking comprise a rim of the outer periphery of a first guidewire holder and a stacking groove of a second guidewire holder. The rim and groove are coupled to cause the second guidewire holder to be stacked on the first guidewire holder. The operation of a stacking groove and a rim in interconnecting multiple guidewire holders is explained more fully hereafter. Stacking the guidewire holders is beneficial because it reduces the amount of space that the guidewire holders occupy.

Figure 4:
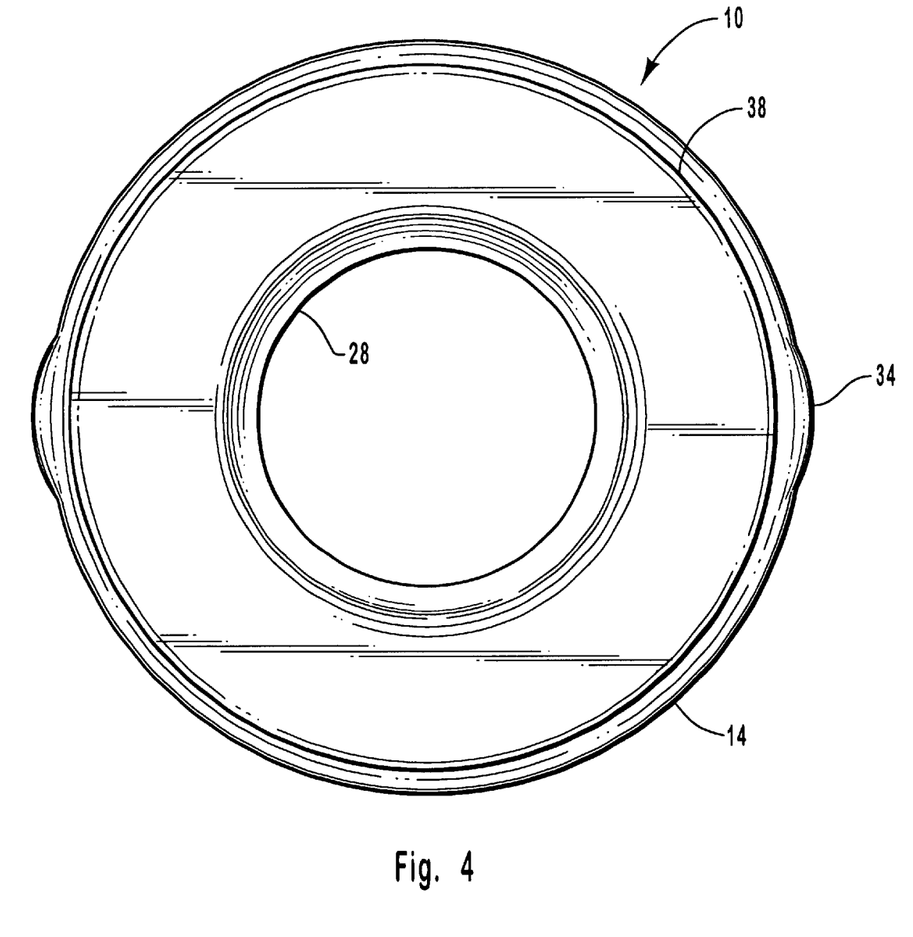
FIG. 4 is bottom planar view of the embodiment of FIG. 1.

With reference to FIG. 4, an illustration is provided of a bottom planar view of the embodiment of FIG. 1. The stacking groove is illustrated in FIG. 4 as stacking groove 38, which is a continuous groove formed on the bottom surface of guidewire holder 10. Stacking groove 38 is designed to be coupled to the rim of the outer periphery of a guidewire holder, such as rim 40 of FIG. 2. Therefore, the shape and size of stacking groove 38 is formed to generally correspond to the shape and size of the rim 40. While the shape of the rim 40 of FIG. 2 is generally circular, embodiments of the present invention embrace other shapes of the rim of the outer periphery of the pan, such as, for example a generally oval, triangular or rectangular shape. However, in order for a second guidewire holder to be stacked on top of a first guidewire holder, the shape of the stacking groove formed on the bottom surface of the second guidewire holder generally matches or corresponds to the shape of the rim of the first guidewire holder where the means for stacking comprises a stacking groove coupled to a rim of an outer periphery. The embodiments of the present invention also embrace other means for stacking that allows guidewire holders to be stacked on top of each other. Such means for stacking may be implemented via a wide variety of structures that allow the guidewire holders to be stacked in a wide variety of orientations.

Figure 5:
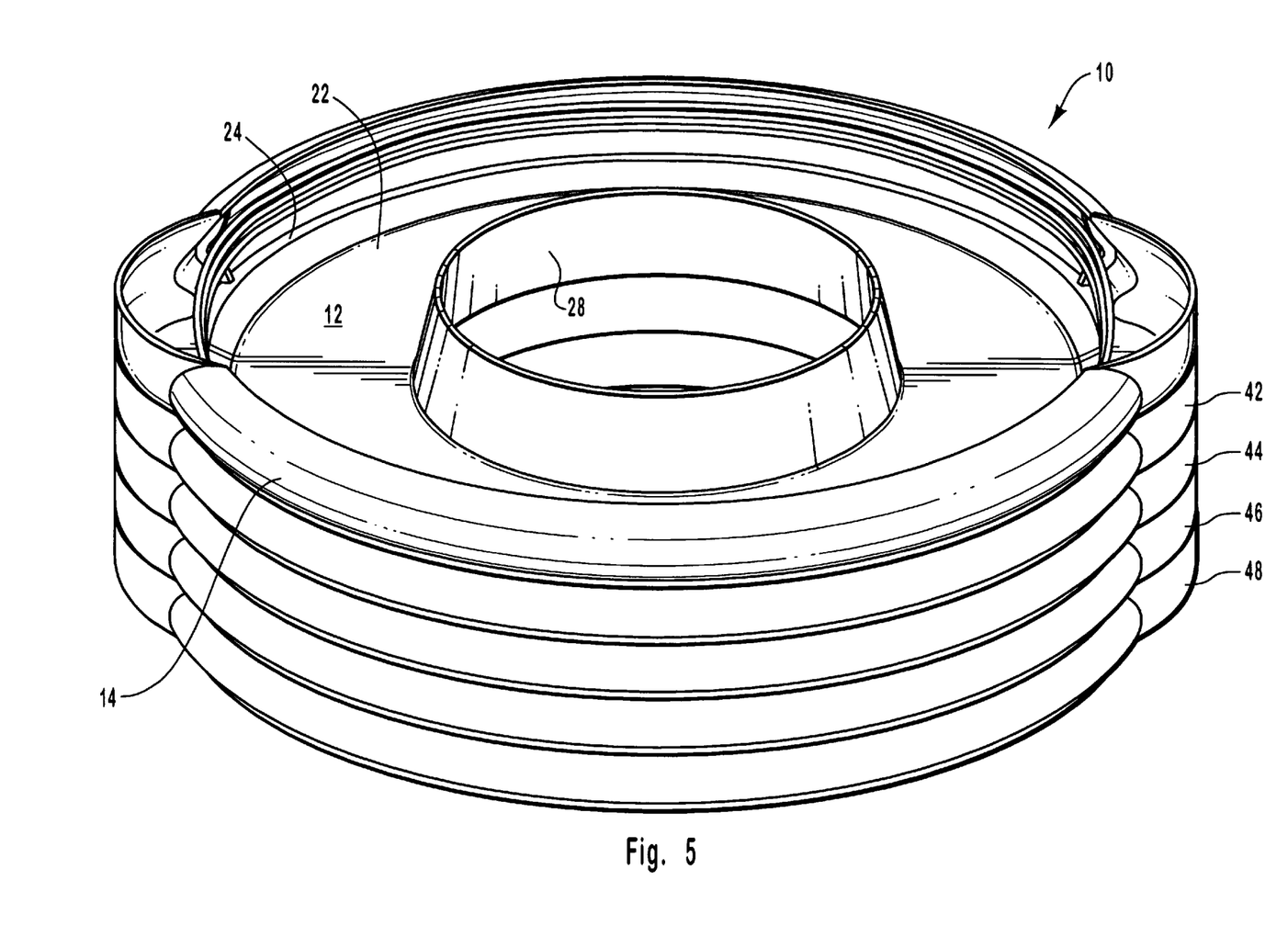
FIG. 5 is a perspective view of the embodiment of FIG. 1, illustrating multiple guidewire holders stacked on top of each other.

Referring next to FIG. 5, a perspective view is illustrated of a variety of guidewire holders in a stacked orientation to implement a means for stacking that allow the guidewire holders to be stacked. In FIG. 5, the guidewire holder 10 is illustrated as retaining guidewire 30 and is stacked on top of guidewire holder 42, which is stacked on top of guidewire holder 44, which is stacked on top of guidewire holder 46, which is stacked on top of guidewire holder 48. Each of the guidewire holders 42–48 are also configured to be able to retain a corresponding guidewire (not shown). As provided above, the guidewire holders are able to be stacked due to a means for stacking that comprises, for example, a stacking groove from one guidewire holder and a rim of an outer periphery of another guidewire holder. Thus, to form the stacking orientation of guidewire holders 10, and 42–48 as illustrated in FIG. 5, the stacking groove of the bottom surface of guidewire holder 10 is coupled with at least a portion of the rim of the outer periphery of guidewire holder 42, the stacking groove of the bottom surface of guidewire holder 42 is coupled with at least a portion of the rim of the outer periphery of guidewire holder 44, the stacking groove of the bottom surface of guidewire holder 44 is coupled with at least a portion of the rim of the outer periphery of guidewire holder 46, and the stacking groove of the bottom surface of guidewire holder 46 is coupled with at least a portion of the rim of the outer periphery of guidewire holder 48.

Thus, the present invention relates to a stackable holder for storage and retrieval of a coiled wire. More specifically, the present invention is directed to a stackable holder for storage and retrieval of a coiled medical guidewire, wherein the stackable holder facilitates the extraction of the coiled guidewire from the holder. The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A guidewire holder for storage and retrieval of a coiled guidewire, the guidewire holder comprising:
   means for defining a pan that holds a coiled guidewire; and
   means for retaining the coiled guidewire within the pan, wherein said means for retaining comprises a first rib and a concave inner wall of an outer periphery of said means for defining a pan.

2. A guidewire holder as recited in claim 1, wherein the coiled guidewire is substantially retained at the concave inner wall.

3. A guidewire holder as recited in claim 2, wherein the first rib comprises a slot for receiving a first portion of the coiled guidewire.

4. A guidewire holder as recited in claim 3, further comprising means for providing access to the coiled guidewire, wherein said means for providing access suspends at least a portion of the coiled guidewire away from the outer periphery of the pan.

5. A guidewire holder as recited in claim 4, wherein said means for providing access is formed in the outer periphery of the pan.

6. A guidewire holder as recited in claim 5, wherein said means for providing access comprises a set of ribs and a nose portion, wherein the first rib is one of the set of ribs.

7. A guidewire holder as recited in claim 6, further comprising a means for stacking.

8. A guidewire holder as recited in claim 7, wherein said means for stacking comprises a stacking groove formed on the bottom surface of the pan and a rim of the outer periphery of the pan.

9. A guidewire holder as recited in claim 8, wherein the pan further comprises an inner periphery.

10. A guidewire holder as recited in claim 9, further comprising means for holding the pan that comprises the outer periphery and the inner periphery of the pan.

11. A guidewire holder as recited in claim 10, wherein the pan further comprises an annular channel and an annular ridge.

12. A guidewire holder as recited in claim 11, wherein the coiled guidewire is retained so as to be substantially immersed in a storage fluid.

13. A guidewire holder as recited in claim 12, wherein the inner periphery reduces an amount of the storage fluid that is contained in the pan.

14. A guidewire holder as recited in claim 13, wherein the pan comprises at least one of a polymer and a metal.

15. A guidewire holder for storage and retrieval of a coiled guidewire, the guidewire holder comprising:
   means for defining a pan that holds a coiled guidewire and storage fluid, wherein the pan comprises a floor and an outer periphery having a concave inner wall and one or more ribs;
   means for retaining the coiled guidewire within the pan, wherein said means for retaining comprises the concave inner wall and the one or more ribs, and wherein said means for retaining holds the coiled guidewire substantially immersed in the storage fluid; and
   means for providing access to the coiled guidewire for removal of the coiled guidewire from the pan, wherein said means for providing access is formed in the outer periphery of the pan.

16. A guidewire holder as recited in claim 15, further comprising:
   means for stacking the guidewire holder; and
   means for holding the pan, wherein said means for stacking and said means for holding are formed in said means for defining a pan.

17. A guidewire holder as recited in claim 16, wherein said means for providing access causes a portion of the coiled guidewire to be suspended away from the outer periphery.

18. A guidewire holder as recited in claim 17, wherein said means for providing access comprises a nose portion formed in the outer periphery of the pan to suspend the suspended portion of the coiled guidewire away from the outer periphery of the pan.

19. A guidewire holder as recited in claim 18, wherein said means for providing access further comprises a set of ribs to assist in suspending the suspended portion of the coiled guidewire, and wherein the set of ribs are of the one or more ribs of the outer periphery.

20. A guidewire holder as recited in claim 19, wherein each of the one or more ribs comprises a slot that receives a portion of the coiled guidewire.

21. A guidewire holder as recited in claim 20, wherein said means for stacking comprises:
   a continuous stacking groove formed in the bottom surface of the pan; and
   a rim of the outer periphery.

22. A guidewire holder as recited in claim 21, wherein said means for holding comprises the outer periphery and a continuous inner periphery of the pan.

23. A guidewire holder as recited in claim 22, wherein the continuous inner periphery reduces an amount of the storage fluid that is contained in the pan.

24. A guidewire holder for storage and retrieval of a coiled guidewire, the guidewire holder comprising:
- a pan floor;
- an outer periphery coupled to said pan floor that retains a coiled guidewire within said outer periphery, wherein said outer periphery comprises a concave inner wall; and
- a nose portion formed in said outer periphery that suspends at least a portion of the coiled guidewire away from said outer periphery.

25. A guidewire holder as recited in claim 24, wherein said outer periphery further comprises one or more ribs, wherein a slot is formed in each of the one or more ribs to receive a portion of the coiled guidewire.

26. A guidewire holder as recited in claim 25, further comprising an inner periphery coupled to said pan floor, wherein a combination of said outer periphery and said inner periphery forms a handle.

27. A guidewire holder as recited in claim 26, wherein said outer periphery retains the coiled guidewire substantially immersed in storage fluid.

28. A guidewire holder as recited in claim 24, further comprising a stacking groove formed in a bottom surface of the pan, wherein the stacking groove substantially corresponds to a size and shape of a rim of said outer periphery.

29. A guidewire holder as recited in claim 24, wherein said pan floor comprises an annular ridge and an annular channel, and wherein the annular channel is coupled to said inner periphery and the annular ridge is interposed between the annular channel and said outer periphery.

30. A guidewire holder for storage and retrieval of a coiled guidewire, the guidewire holder comprising:
- a pan floor;
- an outer periphery coupled to said pan floor that retains a coiled guidewire substantially immersed in storage fluid within said outer periphery, wherein said outer periphery comprises a concave inner wall; and
- an inner periphery coupled to said pan floor, wherein a combination of said outer periphery and said inner periphery creates a handle.

31. A guidewire holder as recited in claim 30, wherein said outer periphery further comprises one or more ribs, wherein a slot is formed in each of the one or more ribs to receive a portion of the coiled guidewire.

32. A guidewire holder as recited in claim 31, further comprising a nose portion formed in said outer periphery that suspends at least a portion of the coiled guidewire away from said outer periphery.

33. A guidewire holder as recited in claim 32, further comprising a stacking groove formed in a bottom surface of the pan, wherein the stacking groove substantially corresponds to a size and shape of a rim of said outer periphery.

34. A guidewire holder as recited in claim 33, wherein said pan floor comprises an annular ridge and an annular channel, and wherein the annular channel is coupled to said inner periphery and the annular ridge is interposed between the annular channel and said outer periphery.

35. A system for stacking a plurality of guidewire holders, wherein each of the plurality of guidewire holders is configured to be able to receive and retain a coiled guidewire therein, the system comprising:
- a rim of an outer periphery of a first guidewire holder, wherein the outer periphery comprises a concave inner wall; and
- a stacking groove formed in a bottom surface of a second guidewire holder to correspond to a size and shape of said rim, wherein said stacking groove and said rim are coupled to allow the second guidewire holder to be stacked on top of the first guidewire holder.

36. A system as recited in claim 35, wherein the shape of said stacking groove is continuous.

37. A system as recited in claim 36, wherein the shape of said stacking groove is substantially circular.

* * * * *

UNITED STATES PATENT AND TRADEMARK OFFICE
CERTIFICATE OF CORRECTION

PATENT NO. : 6,547,072 B2 Page 1 of 1
DATED : April 15, 2003
INVENTOR(S) : John Whiting, Jim Mottola and Fred Lampropoulos It is certified that error appears in the above-identified patent and that said Letters Patent is hereby corrected as shown below:

<u>Column 7,</u>
Line 31, change "illustrated" to -- illustrative --

Signed and Sealed this

Ninth Day of December, 2003

JAMES E. ROGAN
*Director of the United States Patent and Trademark Office*